(12) United States Patent
Silverman

(10) Patent No.: US 8,135,546 B2
(45) Date of Patent: Mar. 13, 2012

(54) MOMENT ANALYSIS OF TERTIARY PROTEIN STRUCTURES

(75) Inventor: Benjamin David Silverman, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 447 days.

(21) Appl. No.: 11/931,296

(22) Filed: Oct. 31, 2007

(65) Prior Publication Data
US 2008/0071510 A1    Mar. 20, 2008

Related U.S. Application Data

(62) Division of application No. 10/616,880, filed on Jul. 10, 2003, now Pat. No. 8,024,126.

(51) Int. Cl.
G01N 31/00 (2006.01)
G01N 33/48 (2006.01)
G06F 17/50 (2006.01)
G06F 7/60 (2006.01)

(52) U.S. Cl. .......... 702/27; 702/19; 702/22; 703/1; 703/2

(58) Field of Classification Search .......... None
See application file for complete search history.

(56) References Cited

U.S. PATENT DOCUMENTS
5,784,294 A * 7/1998 Platt et al. .......... 702/27

OTHER PUBLICATIONS

Eisenberg et al. A helical hydrophobic moment: a measure of the amphiphilicity of a helix. Nature, 1982, vol. 299, pp. 371-374.*
Silverman, B.D., "Hydrophobic Moments of Protein Structures: Spatially Profiling the Distribution," PNAS, vol. 98, No. 9, pp. 4996-5001 (Apr. 24, 2001).
Silverman B.D., "A Two-Component Nucleation Model of Protein Hydrophobicity," J. Theor. Biol., vol. 216, pp. 139-146 (2002).
Silverman, B.D., "Hydrophobicity of Transmembrane Proteins: Spatially Profiling the Distribution," Protein Science, 12:586-599 (2003).

* cited by examiner

*Primary Examiner* — Russell S Negin
(74) *Attorney, Agent, or Firm* — Ryan, Mason & Lewis, LLP (57) ABSTRACT

Techniques for analyzing protein structures, such as a tertiary protein structure, are provided. A centroid of the residue centroids is calculated. The centroid of the residue centroids is used as a spatial origin of a global linear hydrophobic moment. The correlation between residue centroid magnitude and residue solvent accessibility is enhanced. The global linear hydrophobic moment is defined, wherein each of the residue centroids contributes a magnitude and direction to the global linear hydrophobic moment. A method for comparing at least two tertiary protein structures is also disclosed.

18 Claims, 7 Drawing Sheets

FIG. 3    CORRELATION COEFFICIENTS OF ELLIPSOIDAL AND RADIAL DISTANCES WITH SOLVENT ACCESSIBILITIES

| PROTEIN | RESIDUE NUMBER | ELLIPSOIDAL | RADIAL | $g'_2$ | $g'_3$ | PROTEIN | RESIDUE NUMBER | ELLIPSOIDAL | RADIAL | $g'_2$ | $g'_3$ |
|---|---|---|---|---|---|---|---|---|---|---|---|
| 1CDZ | 96 | 0.852 | 0.795 | 1.56 | 1.66 | 1AUN | 208 | 0.672 | 0.644 | 1.03 | 1.39 |
| 2RAC | 105 | 0.830 | 0.788 | 1.29 | 1.46 | 1LBU | 213 | 0.632 | 0.566 | 1.70 | 1.93 |
| 1YCC | 108 | 0.821 | 0.776 | 1.31 | 1.50 | 1YAL | 216 | 0.756 | 0.685 | 1.58 | 1.77 |
| 1NEU | 115 | 0.782 | 0.669 | 1.93 | 2.04 | 2ACT | 218 | 0.744 | 0.657 | 1.58 | 1.75 |
| 1DLW | 116 | 0.769 | 0.700 | 1.40 | 1.55 | 1EUG | 219 | 0.734 | 0.686 | 1.28 | 1.60 |
| 1BLO | 116 | 0.752 | 0.575 | 2.40 | 2.60 | 1AKZ | 223 | 0.736 | 0.677 | 1.33 | 1.59 |
| 1DZO | 120 | 0.702 | 0.517 | 2.48 | 2.89 | 1UDH | 228 | 0.760 | 0.703 | 1.39 | 1.63 |
| 1QTS | 123 | 0.815 | 0.653 | 2.16 | 2.21 | 1TPH | 245 | 0.744 | 0.712 | 1.11 | 1.40 |
| 1A4V | 123 | 0.783 | 0.686 | 1.87 | 1.99 | 1G6V | 256 | 0.754 | 0.735 | 1.21 | 1.31 |
| 3LZT | 129 | 0.792 | 0.682 | 1.75 | 1.86 | 1BN1 | 257 | 0.733 | 0.719 | 1.22 | 1.31 |
| 1PDO | 122 | 0.831 | 0.800 | 1.25 | 1.45 | 2DRI | 271 | 0.647 | 0.455 | 2.48 | 2.55 |
| 2SNS | 141 | 0.788 | 0.757 | 1.34 | 1.51 | 1AUA | 296 | 0.620 | 0.534 | 1.40 | 1.48 |
| 1ATO | 145 | 0.780 | 0.737 | 1.18 | 1.48 | 1A3H | 300 | 0.739 | 0.726 | 1.17 | 1.25 |
| 1H97 | 147 | 0.689 | 0.608 | 1.50 | 1.79 | 1LDM | 309 | 0.690 | 0.623 | 1.63 | 1.78 |
| 1A6M | 151 | 0.728 | 0.676 | 1.19 | 1.61 | 1FSZ | 318 | 0.715 | 0.641 | 1.60 | 1.69 |
| 1I1B | 151 | 0.847 | 0.825 | 1.14 | 1.26 | 1KFU | 338 | 0.625 | 0.473 | 2.23 | 2.41 |
| 1CO2 | 153 | 0.724 | 0.670 | 1.13 | 1.56 | 1UBY | 348 | 0.578 | 0.481 | 1.48 | 1.89 |
| 1PHR | 154 | 0.818 | 0.795 | 1.12 | 1.35 | 1A26 | 351 | 0.655 | 0.612 | 1.19 | 1.52 |
| 1CZT | 160 | 0.817 | 0.762 | 1.56 | 1.66 | 1CTN | 356 | 0.651 | 0.620 | 1.11 | 1.39 |
| 121P | 166 | 0.763 | 0.742 | 1.13 | 1.20 | 1PHC | 405 | 0.573 | 0.524 | 1.21 | 1.61 |
| 1E6C | 170 | 0.704 | 0.666 | 1.44 | 1.83 | 1GAI | 448 | 0.703 | 0.674 | 1.28 | 1.45 |
| 1GKY | 186 | 0.670 | 0.632 | 1.13 | 1.43 | 1BGV | 449 | 0.568 | 0.535 | 1.07 | 1.38 |
| 2KFZ | 195 | 0.759 | 0.722 | 1.23 | 1.47 | 3PBG | 468 | 0.685 | 0.667 | 1.14 | 1.31 |
| 1DZV | 206 | 0.765 | 0.669 | 2.00 | 2.03 | 3COX | 500 | 0.640 | 0.559 | 1.63 | 1.73 |
| 1UCH | 206 | 0.805 | 0.783 | 1.18 | 1.36 | 1FEH | 574 | 0.565 | 0.487 | 1.88 | 2.09 |

MOMENT MAGNITUDES AND MEAN HYDROPHOBICITIES

| PROTEIN | MOMENT MAGNITUDE | RANDOM MAGNITUDE | NUMBER GREATER | MEAN HYDROPHOBICITY | PROTEIN | MOMENT MAGNITUDE | RANDOM MAGNITUDE | NUMBER GREATER | MEAN HYDROPHOBICITY |
|---|---|---|---|---|---|---|---|---|---|
| 1CDZ | 6.16 | 9.49 | 765 | -0.083 | 1AUN | 3.57 | 6.54 | 868 | -0.122 |
| 2RAC | 4.24 | 7.91 | 864 | -0.090 | 1LBU | 3.49 | 6.82 | 878 | -0.135 |
| 1YCC | 7.62 | 8.71 | 580 | -0.222 | 1YAL | 6.58 | 7.32 | 565 | -0.158 |
| 1NEU | 8.91 | 10.24 | 575 | -0.083 | 2ACT | 11.20 | 7.29 | 112 | -0.092 |
| 1DLW | 5.97 | 7.68 | 677 | -0.044 | 1EUG | 5.51 | 7.41 | 695 | -0.064 |
| 1BLO | 5.13 | 10.18 | 869 | -0.164 | 1AKZ | 1.58 | 7.59 | 989 | -0.105 |
| 1DZO | 6.29 | 9.80 | 762 | -0.224 | 1UDH | 6.34 | 7.39 | 605 | -0.065 |
| 1QTS | 3.13 | 10.66 | 977 | -0.063 | 1TPH | 6.92 | 7.00 | 491 | -0.109 |
| 1A4V | 9.95 | 10.64 | 533 | -0.089 | 1G6V | 6.93 | 7.71 | 560 | -0.154 |
| 3LZT | 10.35 | 8.43 | 269 | -0.139 | 1BN1 | 6.38 | 7.62 | 623 | -0.158 |
| 1PDO | 8.87 | 8.40 | 414 | -0.047 | 2DRI | 3.26 | 8.86 | 943 | -0.145 |
| 2SNS | 6.31 | 8.15 | 671 | -0.227 | 1AUA | 17.09 | 7.86 | 6 | -0.134 |
| 1AIO | 10.11 | 8.02 | 242 | -0.069 | 1A3H | 1.83 | 6.57 | 975 | -0.131 |
| 1H97 | 5.22 | 8.94 | 831 | -0.110 | 1LDM | 13.81 | 7.90 | 65 | -0.039 |
| 1A6M | 3.41 | 8.73 | 943 | -0.117 | 1FSZ | 4.83 | 7.48 | 784 | -0.089 |
| 1I1B | 3.92 | 8.76 | 915 | -0.150 | 1KFU | 11.05 | 8.88 | 281 | -0.118 |
| 1CQ2 | 3.79 | 8.47 | 922 | -0.122 | 1UBY | 8.84 | 8.27 | 412 | -0.104 |
| 1PHR | 5.20 | 8.04 | 770 | -0.121 | 1A26 | 5.44 | 7.44 | 725 | -0.117 |
| 1CZT | 9.91 | 9.16 | 395 | -0.120 | 1CTN | 2.78 | 6.73 | 937 | -0.124 |
| 121P | 7.68 | 7.80 | 478 | -0.134 | 1PHC | 3.67 | 7.23 | 880 | -0.087 |
| 1E6C | 9.54 | 8.71 | 366 | -0.054 | 1GAI | 5.79 | 6.07 | 522 | -0.114 |
| 1GKY | 9.63 | 8.43 | 332 | -0.170 | 1BGV | 7.75 | 6.40 | 296 | -0.100 |
| 2KFZ | 6.82 | 8.07 | 594 | -0.096 | 3PBG | 5.82 | 6.34 | 544 | -0.121 |
| 1DZV | 15.31 | 8.41 | 40 | -0.042 | 3COX | 4.32 | 6.95 | 806 | -0.120 |
| 1UCH | 10.39 | 7.90 | 232 | -0.094 | 1FEH | 6.92 | 7.60 | 567 | -0.129 |

FIG. 6

NEUMAIER HYDROPHOBICITY SCALE

| AMINO ACID | HYDROPHOBICITY | AMINO ACID | HYDROPHOBICITY |
|---|---|---|---|
| LYS | −1.00 | HIS | −0.15 |
| ASP | −0.97 | ALA | −0.06 |
| GLU | −0.85 | TYR | 0.35 |
| ARG | −0.80 | CYS | 0.56 |
| GLN | −0.71 | TRP | 0.57 |
| ASN | −0.70 | MET | 0.68 |
| SER | −0.48 | VAL | 0.75 |
| PRO | −0.45 | LEU | 0.83 |
| THR | −0.38 | PHE | 0.99 |
| GLY | −0.32 | ILE | 1.00 |

DEFENSIN AND DEFENSIN LIKE MOMENT MAGNITUDES AND MEAN HYDROPHOBICITIES

| PROTEIN | MOMENT MAGNITUDE | RANDOM MAGNITUDE | NUMBER GREATER | MEAN HYDOPHOBICITY | $g'_2$ | $g'_3$ |
|---------|------------------|------------------|----------------|--------------------|--------|--------|
| 1AHL | 16.86 | 9.09 | 24 | −0.089 | 1.85 | 2.02 |
| 1APF | 23.16 | 10.55 | 31 | −0.100 | 1.20 | 2.66 |
| 1B8W | 15.79 | 18.98 | 539 | −0.182 | 1.97 | 5.34 |
| 1BNB | 13.58 | 17.00 | 615 | −0.001 | 3.13 | 4.96 |
| 1DFN | 3.34 | 9.25 | 955 | 0.070 | 2.29 | 2.44 |
| 1FD3 | 5.74 | 9.35 | 806 | −0.079 | 1.97 | 2.36 |
| 1FJN | 7.02 | 12.37 | 745 | −0.076 | 1.64 | 3.96 |
| 1SH1 | 36.35 | 13.60 | 9 | −0.184 | 1.98 | 3.60 |

MOMENT ANALYSIS OF TERTIARY PROTEIN STRUCTURES

CROSS REFERENCE TO RELATED APPLICATIONS

This application is a Divisional Application of U.S. patent application Ser. No. 10/616,880, filed Jul. 10, 2003, now U.S. Pat. No. 8,024,126, which is incorporated by reference herein.

FIELD OF THE INVENTION

The present invention relates to protein structure analysis and, more particularly, to providing a moment analysis of tertiary protein structures.

BACKGROUND OF THE INVENTION

Proteins are composed of a series of amino acid residues. There are 20 known naturally occurring amino acids. The three-dimensional structure of a protein is typically composed of a series of folded regions. Current research has focused on protein structural determination because three dimensional protein structure is important for all human bodily functions.

Many proteins are globular and form in an aqueous environment. These globular proteins are composed of hydrophobic amino acids that avoid water, and hydrophilic amino acids that are attracted to water. When these proteins fold, the hydrophobic amino acids are predominantly arranged in the non-aqueous center of the protein molecule and the hydrophilic amino acids are arranged on the aqueous protein surface. A protein formed in this manner will have a hydrophobic core and a hydrophilic exterior. In addition to this inside-to-outside radial distribution of hydrophobic and hydrophilic amino acids, there is a gradient of the hydrophobicity of amino acids across the linear extent of the protein. This gradient is important since, in many instances, it points to local regions that are involved in protein function. Many of these protein functional regions consist of a predominance of hydrophilic amino acids. In the binding to lipid bilayers these regions may consist of hydrophobic amino acid residues.

The profile of the spatial distribution of hydrophobic and hydrophilic amino acids from the protein interior to exterior has been performed previously, in B. D. Silverman, *Hydrophobic Moments of Protein Structures—Spatially Profiling the Distribution*, 98 PROC. NATL. ACAD. SCI. 4996-5001 (2001). Previous methods involved the determination of a helical hydrophobic moment that provides a measure of the amphiphilicty of a segment of a secondary protein structure. See for example, D. Eisenberg et al, *The Helical Hydrophobic Moment, a Measure of the Amphiphilicity of a Helix*, 299 NATURE 371-74 (1982); D. Eisenberg et al, *Analysis of Membrane Protein Sequences With the Hydrophobic Moment Plot*, 179 J. MOL BIOL. 125-142 (1984); H. J. Pownall et al, *Helical Amphipathic Moment Application to Plasma Lipoproteins*, 159 FEBS 17-23 (1983); L. Tsigelny et al, *Mechanism of Action of Chromogranin A on Catecholamine Release: Molecular Modeling of the Catestatin Region Reveals a β-strand/loop/β-strand Structure Secured by Hydrophobic Interactions and Predictive of Activity*, 77 REGULATORY PEPTIDES 43-53 (1998); J. P. Pardo et al., *An Alternative Model for the Transmembrane Segments of the Yeast H+-ATPase*, 15 YEAST 1585-93 (1999); P. W. Mobley, *Membrane Interactions of the Synthetic N-terminal Peptide of HIV-1 gp41 and its Structural Analogs*, 1418 BIOCHIMICA ET BIOPHYSICA ACIA, 1-18 (1999); L. Thong et al, *Flexible Programs for the Prediction of Average Amphiphilicity of Multiply Aligned Homologous Proteins Application to Integral Membrane Transport Proteins*, 16 MOLECULAR MEMBRANE BIOLOGY 173-79 (1999); X. Gallet et al., *A Fast Method to Predict Protein Interaction Sites from Sequences*, 302 J. MOL. BIOL. 917-926 (2000); D. A. Phoenix et al., *The Hydrophobic Moment and its Use in the Classification of Amphiphilic Structures (Review)*, 19 MOLECULAR MEMBRANE BIOLOGY 1-10 (2002).

While determination of the hydrophobic moments of secondary structures are useful, it is desirable to have measurements pertaining to the entire protein structure. These measurements would yield information useful in protein structure classification and functional legion determination.

SUMMARY OF THE INVENTION

Techniques for protein structure analysis are provided. In one aspect of the present invention, a method for calculating a moment of a tertiary protein structure comprising a plurality of residues is provided. A centroid of residue centroids is calculated. The centroid of residue centroids is used as a spatial origin of a global linear hydrophobic moment. The correlation between residue centroid magnitude and residue solvent accessibility is enhanced. The global linear hydrophobic moment is defined, wherein each of the residue centroids contributes a magnitude and direction to the global linear hydrophobic moment.

In another aspect of the present invention, a method for comparing at least two tertiary protein structures comprising a plurality of residues is provided. For each tertiary protein structure, the method comprises the following steps. A centroid of residue centroids is calculated. The centroid of residue centroids is used as a spatial origin of a global linear hydrophobic moment. The correlation between residue centroid magnitude and residue solvent accessibility is enhanced. The global linear hydrophobic moment is defined, wherein each of the residue centroids contributes a magnitude and direction to the global linear hydrophobic moment. The global linear hydrophobic moment characterizes an amphiphilicity of each tertiary protein structure. The global linear hydrophobic moment of each tertiary protein structures is used to compare the amphiphilicity of the at least two tertiary protein structures.

A more complete understanding of the present invention, as well as further features and advantages of the present invention, will be obtained by reference to the following detailed description and drawings.

BRIEF DESCRIPTION OF THE DRAWINGS

FIG. 3 is a table containing correlation coefficients of distance and solvent accessibility for soluble globular protein databank (PDB) protein structures;

FIG. 5 is a table containing global linear hydrophobic moment magnitudes for fifty PDB protein structures according to the teachings of the present invention;

DETAILED DESCRIPTION OF PREFERRED EMBODIMENTS

Figure 1:
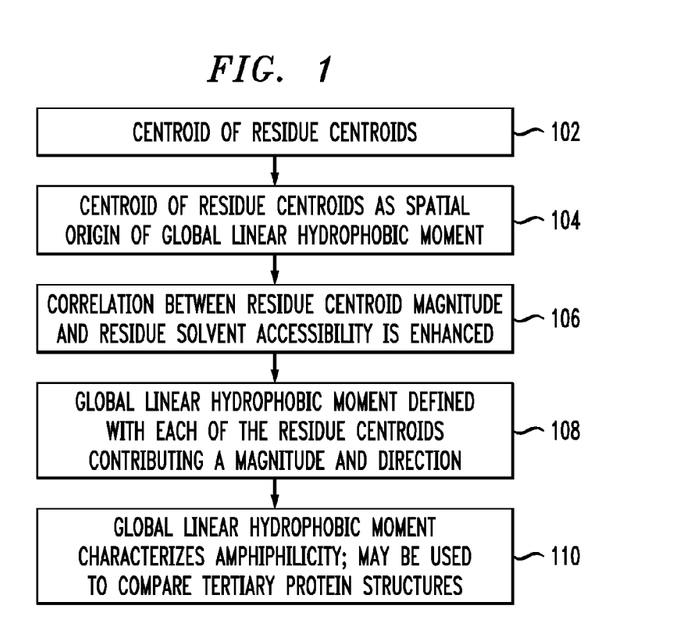
FIG. 1 is a flow chart illustrating an exemplary methodology for calculating a moment of a tertiary protein structure comprising a plurality of residues according to the teachings of the present invention.

FIG. 1 is a flow chart illustrating an exemplary methodology for calculating a moment of a tertiary protein structure comprising a plurality of residues. In step 102 of FIG. 1, a centroid of the residue centroids (hereinafter "residue centroids") is calculated. The centroid of residue centroids may represent a geometric center of the tertiary protein structure. The centroid of a given molecule is determined by setting the mass of each atom of the molecule to a value of one.

The present calculations are based upon the residue locations of the protein. The center-of-geometry of the ith residue, or residue centroid, $\vec{r}_i$, is calculated with inclusion of only the backbone α—carbon atom and exclusion of the hydrogen atoms. This distribution of points in three-dimensional space enables calculation of the geometric center, $\vec{r}_c$, namely, the centroid of the residue centroids;

$$\vec{r}_c = \frac{1}{n}\sum_i \vec{r}_i, \qquad [1]$$

wherein n is the total number of residues.

Linear hydrophobic imbalance about the average value of protein hydrophobicity, $\bar{h}$, is given by the following first-order hydrophobic moment:

$$\vec{h}_1 = \frac{1}{n}\sum_i (h_i - \bar{h})\vec{r}_i, \qquad [2]$$

wherein $\vec{h}_1$, is invariant with respect to the choice of the origin of the moment expansion since the subtraction of the mean of the distribution yields a distribution, $(h_i - \bar{h})$, with vanishing zero-order moment. The origin of the distribution, $h_i$, that yields the value of $\vec{h}_1$ in Equation 2, is the residue centroids, $\vec{r}_c$. Namely, $$\bar{h} = \frac{1}{n}\sum_i h_i,$$

enables Equation 2 to be written as:

$$\vec{h}_1 = \frac{1}{n}\sum_i h_i(\vec{r}_i - \vec{r}_c). \qquad [3]$$

The first-order hydrophobic imbalance about the mean value of hydrophobicity is therefore given by a global linear hydrophobic moment calculated with the centroid of the residue centroids as origin. Thus, as shown in step 104 of FIG. 1, the centroid of residue centroids is used as a spatial origin of the global linear hydrophobic moment. Identification of the spatial origin of the global linear hydrophobic moment expansion enables explicit registration of the global linear hydrophobic moment with the underlying tertiary protein structure.

An ellipsoidal characterization of protein shape is obtained by defining a second rank geometric tensor as follows:

$$\tilde{G} = \sum_i \left( \tilde{1}|\vec{r}_i - \vec{r}_c|^2 - (\vec{r}_i - \vec{r}_c)(\vec{r}_i - \vec{r}_c) \right), \qquad [4]$$

wherein $\tilde{1}$, the unit dyadic, is diagonalized to provide the moments-of-geometry, $g_1$, $g_2$ and $g_3$. These moments-of-geometry are the moments-of-inertia of a discrete distribution of points of unit mass. The moments-of-geometry are lineally related to the moments described in M. H. Hao et al, *Effects of Compact Volume and Chain Stiffness on the Conformations of Native Proteins*, 89 PROC NATL. ACAD. SCI. 6614-18 (1992), the disclosure of which is incorporated by reference herein, obtained by writing the geometric tensor in a more symmetric form.

The aspect ratios of the moments-of-geometry provide an ellipsoidal characterization of protein shape:

$$g_1 x_p^2 + g_2 y_p^2 + g_3 z_p^2 = d^2, \qquad [5]$$

wherein $x_p$, $y_p$, $z_p$, are coordinates in the frame of the principal axes with the centroid of the protein structure as origin. If the magnitudes are ordered as:

$$g_1 < g_2 < g_3, \qquad [6]$$

then the major principal axis is of extent, $d^2/g_1$, wherein each ith residue at location $x_{ip}$, $y_{ip}$, $z_{ip}$, in the principal axis flame, can be considered to reside on an ellipsoid with major principal axis equal to $d_i^2/g_1$, namely:

$$g_1 x_{ip}^2 + g_2 y_{ip}^2 + g_3 z_{ip}^2 = d_i^2 \qquad [7]$$

For a compact protein, the residue with the largest $d_i$ can specify the ellipsoid defining a presumed protein surface. Residues with the same $d_i$, namely, residues residing on the same ellipsoid axe at the same radial fractional distance from the protein centroid to the protein ellipsoidal surface Rewriting Equation 7 as:

$$x_{ip}^2 + g_2'y_{ip}^2 + g_3'z_{ip}^2 = d_i'^2, \quad [8]$$

with $$g_2' = g_2/g_1; g_3' = g_3/g_1; d_i'^2 = d_i^2/g_1, \quad [9]$$

enables $d'_i$ to be used as the measure of the radial factional distance of the ith residue from the center of the protein to the protein surface.

Figure 2:
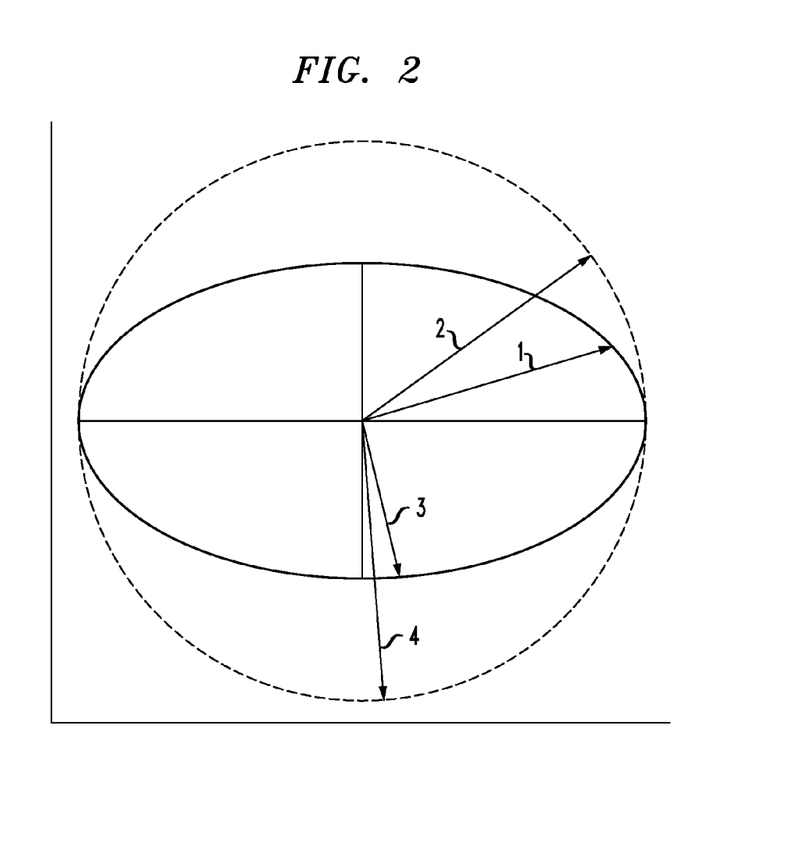
FIG. 2 is a diagram illustrating level arm dependence of a hydrophobic moment according to the teachings of the present invention.

The correlation between residue centroid magnitude and residue solvent accessibility is enhanced, as shown in step 106 of FIG. 1. An exemplary embodiment for enhancing the correlation between residue centroid magnitude and residue solvent accessibility is described below in conjunction with the description of FIG. 2. Thus, when defining the global linear hydrophobic moment, each residue centroid contributes a magnitude and direction to the global linear hydrophobic moment, as shown in step 108 of FIG. 1. Further, as will be addressed in conjunction with the description of FIG. 2, each residue centroid having the same fractional distance to the surface of the tertiary protein structure will contribute an equivalent magnitude to the global linear hydrophobic moment. An accurate determination of the magnitude of the global linear hydrophobic moment is important, as the global linear hydrophobic moment may further be used to compare tertiary protein structures, as shown in step 110 of FIG. 1, and as will be described in detail below. Therefore, one feature that should be modified in Equation 3 is the lever arm dependence of each hydrophobic moment. FIG. 2 is a diagram illustrating level arm dependence of a hydrophobic moment. As can be seen in FIG. 2, a residue near the exterior of a protein and also near the major principal axis is at a greater distance from the center of the protein than a residue near the exterior of the protein but near the minor principal axis. For example, distances from the center of the protein to two residues at different locations on the same ellipsoid, e.g., residing on the same ellipsoidal surface, are denoted by arrows 1 and 3 in FIG. 2. Even though the two residues are at the same fractional distance to the protein surface, the distance from the origin is different. The two residues would therefore make different contributions to the magnitude of the vector, $\vec{r}_i$, in Equation 3. This difference can be corrected based on a spatial linear moment of each residue by mapping the ellipsoidal coordinates onto a sphere with radius equal to the major principal axis. Both locations are then mapped to the positions designated by arrows 2 and 4 in FIG. 2. Since each residue then has an approximately equivalent magnitude, it may be assumed that they contribute an equal magnitude to the global linear hydrophobic moment. With this mapping Equation 3 is written as:

$$\vec{h}_i = \frac{1}{n}\sum_i h_i\left(x_i\hat{i} + \sqrt{g_2'}\,y_i\hat{j} + \sqrt{g_3'}\,z_i\hat{k}\right), \quad [10]$$

wherein $\hat{i}$, $\hat{j}$, $\hat{k}$, are unit vectors along the directions of the principal axes. Since Equation 10 is written in the frame of the principal axes, $\vec{r}_c$ is at the origin and does not shift with the mapping.

This mapping places all residues on the same ellipsoid at the same distance from the center of the protein. This distance metric had been described in B. D. Silverman, *Hydrophobic Moments of Protein Structures, Spatially Profiling the Distribution*, 98 PROC. NATL ACAD. SCI. 4996-5001 (2001) (hereinafter "Silverman"), the disclosure of which is incorporated by reference herein, in regard to calculating the distribution of residue hydrophobicity from the protein interior to the protein exterior. The distance metric correlates more closely with residue solvent accessibility, i.e., the solvent-accessible surface area of each residue, than the residue distance from the ellipsoidal center prior to the mapping. As such, residue centroid magnitude differences which awe not representative of residue solvent accessibility may be corrected for FIG. 3 is a table containing correlation coefficients of distance and solvent accessibility for soluble globular protein databank (PDB) protein structures. FIG. 3 further contains the scaled moments-of-geometry, $g'_2$ and $g'_3$, for fifty soluble globular PDB protein structures. The correlation coefficients obtained with the distances mapped to a sphere are designated "ellipsoidal" while those obtained with the distances from the center of the ellipsoid to the residue ate designated "radial" Residue solvent accessibility was obtained from the web site of the Sealy Center for Structural Biology, University of Texas Medical Branch, Galveston, Tex. Residue solvent accessibility is described, for example, in R. Fraczkiewicz et al, *A New Efficient Algorithm for Calculating Solvent Accessible Surface Areas of Macromolecules*, ECCC3, Northern Illinois University (Nov. 1996), the disclosure of which is incorporated by reference herein. It is important to note that the ellipsoidal correlation coefficients are not only greater than the radial correlation coefficients for every one of the fifty proteins, but that the difference is greatest for the proteins exhibiting the greatest deviations from sphericity.

There are other distance metrics that correlate more closely with residue solvent exposure than the ellipsoidal metric, the distance between the residue centroid and presumed ellipsoidal protein surface. Such other distance metrics, however, do not provide a single origin or location for the moment expansion about which hydrophobic imbalance can be calculated enabling alignment with the tertiary protein structure.

Alternatively, a global hydrophobic vector could be constructed utilizing only vector magnitudes dependent upon the values of residue solvent exposure, $p_i$, and hydrophobicity, $h_i$, and wherein the unit vector, $\hat{\mu}_i$, is defined as:

$$\hat{\mu}_i = (\hat{i}x_i + \hat{j}y_i + \hat{k}z_i)/(x_i^2 + y_i^2 + z_i^2)^{1/2} \quad (11)$$

With Cartesian coordinates $x_i$, $y_i$, $z_i$ written with the centroid of the residue centroids as origin, the following hydrophobic vector can be defined:

$$\vec{H} = \frac{1}{n}\sum_i h_i p_i \hat{\mu}_i. \quad (12)$$

The magnitude of the vector to the ith residue is then weighted solely by the values of the residue solvent exposure, $p_i$, and hydrophobicity, $h_i$, a solvent accessibility metric. Hydrophobic vectors exhibiting significant amphiphilicity, calculated in this manner; will qualitatively correspond to the vectors calculated by the spatial linear moment of Equation 10. As shown in FIG. 3, residue solvent exposure and ellipsoidal distance correlate fairly closely. However, with such choice of origin for the calculation, Equation 12 is not a global linear hydrophobic moment and cannot be recast into a form that is a linear invariant about the mean value of residue hydrophobicity.

Figure 4:
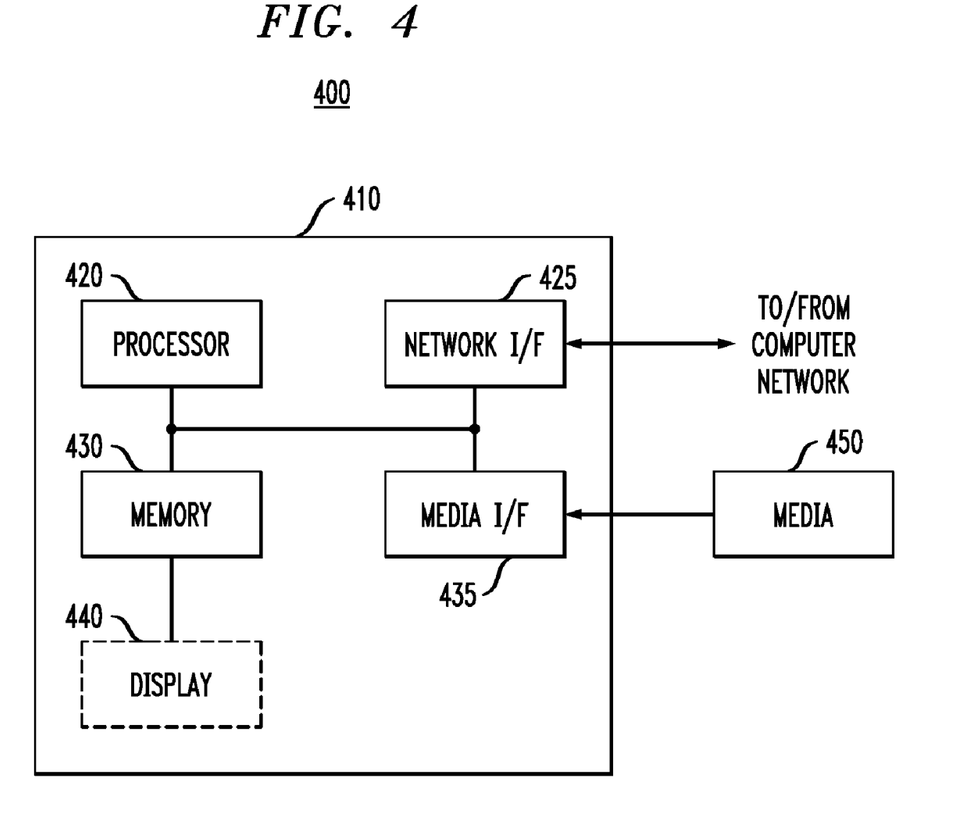
FIG. 4 is a block diagram of an exemplary hardware implementation of a method fox calculating a moment of a tertiary protein structure comprising a plurality of residues according to the teachings of the present invention.

FIG. 4 is a block diagram of an exemplary hardware implementation of a tertiary protein structure analyzer 400 in accordance with one embodiment of the present invention. It is to be understood that apparatus 400 may implement the methodology described above in conjunction with the description of FIG. 1. Apparatus 400 comprises a computer system 410 that interacts with media 450. Computer system 410 comprises a processor 420, a network interface 425, a memory 430, a media interface 435 and an optional display 440. Network interface 425 allows computer system 410 to connect to a network, while media interface 435 allows computer system 410 to interact with media 450, such as a Digital Versatile Disk (DVD) or a hard drive.

As is known in the art, the methods and apparatus discussed herein may be distributed as an article of manufacture that itself comprises a computer-readable medium having computer-readable code means embodied thereon. The computer-readable program code means is operable, in conjunction with a computer system such as computer system 410, to carry out all or some of the steps to perform the methods or create the apparatus discussed herein. The computer-readable code is configured to calculate a centroid of residue centroids; use the centroid of residue centroids as a spatial origin of a global linear hydrophobic moment; enhance correlation between residue centroid magnitude and residue solvent accessibility; and define the global linear hydrophobic moment, wherein each of the residue centroids contributes a magnitude and direction to the global linear hydrophobic moment. The computer-readable medium may be a recordable medium (e g., floppy disks, hard drive, optical disks such as a DVD, or memory cards) or may be a transmission medium (e g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic medium or height variations on the surface of a compact disk.

Memory 430 configures the processor 420 to implement the methods, steps, and functions disclosed herein, The memory 430 could be distributed or local and the processor 420 could be distributed or singular. The memory 430 could be implemented as an electrical, magnetic or optical memory, or any combination of these or other types of storage devices. Moreover, the term "memory" should be construed broadly enough to encompass any information able to be read from or written to an address in the addressable space accessed by processor 420. With this definition, information on a network, accessible through network interface 425, is still within memory 430 because the processor 420 can retrieve the information from the network. It should be noted that each distributed processor that makes up processor 420 generally contains its own addressable memory space. It should also be noted that some or all of computer system 410 can be incorporated into an application-specific or general-use integrated circuit.

Optional video display 440 is any type of video display suitable for interacting with a human user of apparatus 400. Generally, video display 440 is a computer monitor or other similar video display.

As was described above in conjunction with the description of FIG. 1, the global linear hydrophobic moment may be used to compare protein structures. The global linear hydrophobic moment is analogous to the dipole moment for the entire tertiary protein structure. Defining a global linear hydrophobic moment would yield a dual measure comprised of the magnitude and direction of protein ampliphilicity. Thus, the global linear hydrophobic moment characterizes the amphiphilicity of the protein. With such a measure, a simple comparison of the hydrophobic imbalance, or amphiphilicity, of different protein structures could be made. For example, two structures with the same fold and close in root mean square deviation (RMSD) might exhibit very different degrees of overall hydrophobic organization. Such differences would be concisely summarized by the global linear hydrophobic moment. The direction of such moment may also assist in identifying regions of functional interest. Further, in regards to global structural representations of proteins, such as RMSD and radius of gyration, the global linear hydrophobic moment may be useful in the comparison and classification of overall protein hydrophobic organization.

The magnitudes and directions of the global linear hydrophobic moments of interacting proteins can also provide a measure of the hydrophobic imbalance arising from protein to protein interactions. For example, the global linear hydrophobic moments of spatially adjacent protein domains have been shown to provide a quantitative measure of the degree of prevalence of hydrophobic residues in the region of protein domain contact. See R. Zhou et al. *Hydrophobicity of Protein Domains Spatially Profiling Their Distribution*, DISCRETE MATHEMATICS & THEORETICAL COMPUTER SCIENCE (DIMACS) WORKSHOP, (Feb. 27-28, 2003); R. Zhou et al., *Spatial Profiling of Protein Hydrophobicity Native vs Decoy Structures*, RESEARCH IN COMPUTATIONAL MOLECULAR BIOLOGY (RECOMB) (Berlin 2003), the disclosures of which are incorporated by reference herein. Molecular moments, such as global linear hydrophobic moments, may be used to characterize an interesting feature of protein-RNA interactions. The ease and ability to rapidly classify lower order angular arrangements of protein hydrophobicity is useful in connection with generating three-dimensional protein structures.

FIG. 5 is a table containing global linear hydrophobic moment magnitudes for fifty PDB protein structures. The global linear hydrophobic moment magnitudes in FIG. 5 were obtained using Equation 10 for each of the fifty protein structures. The values shown have been multiplied by a factor of ten. To provide a measure for comparison of the linear hydrophobic imbalance, 1,000 calculations have been performed for each protein structure with the amino acid distribution randomized. The average global lineal hydrophobic moment obtained for the 1,000 runs is given in FIG. 5, designated as "random magnitude," together with the number of runs that yielded a magnitude of the moment that was greater than the magnitude of the moment calculated for the native amino acid distribution, designated as "number greater."

Also provided in FIG. 5, is the mean value of hydrophobicity of each protein based on the Neumaier hydrophobicity scale, the scale used in the calculations. The Neumaier hydrophobicity scale will be described below in conjunction with the description of FIG. 6. The signs of the amino acid hydrophobicity values have been reversed for consistency with the calculations described in Silverman. The amino acid hydrophobicity values provide a relative measure of the overall hydrophilicity of the different proteins.

It may be noted from FIG. 5, that most of the values of the moment magnitudes fall in a range of values that are either less than or not significantly different tom a range of values expected for a random distribution of residues. The protein with the greatest magnitude of the global linear hydrophobic moment is 1AUA. The value of the magnitude of this global linear hydrophobic moment is 17.09. One thousand runs with randomization of the amino acid distribution resulted in only six runs with a global linear hydrophobic moment of greater magnitude.

Figure 6:
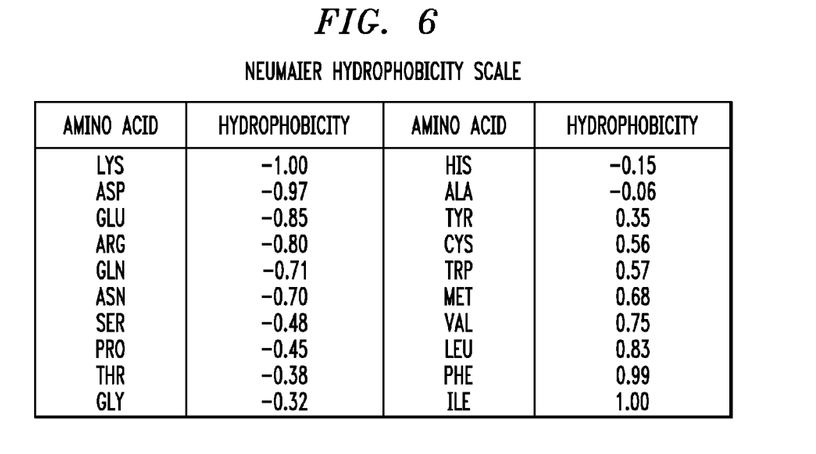
FIG. 6 is a table containing protein hydrophobicity values according to the Neumaier hydrophobicity scale.
Figure 7A:
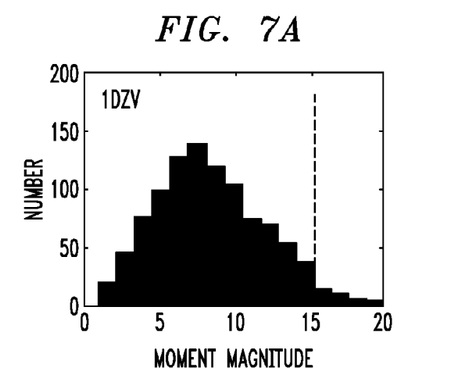
FIGS. 7A-D are histograms illustrating random distributions of global linear hydrophobic moment magnitudes and relationship to four native moments that exhibit significant amphiphilicity according to the teachings of the present invention.
Figure 7B:
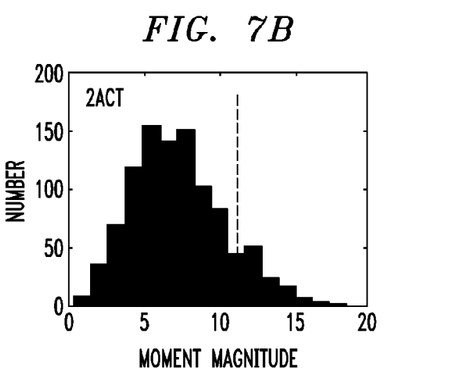
Figure 7C:
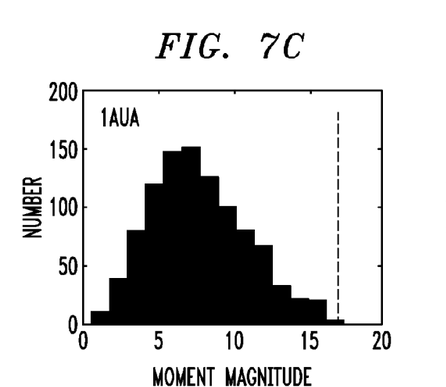
Figure 7D:
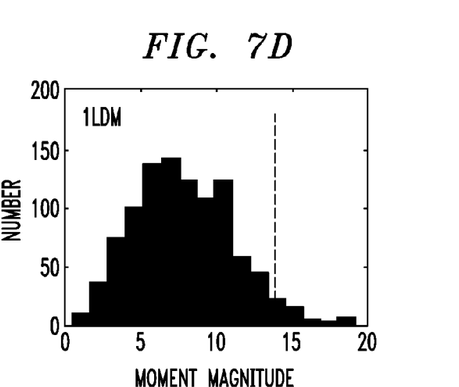

FIG. 6 is a table containing protein hydrophobicity values according to the Neumaier hydrophobicity scale. The Neumaier hydrophobicity scale shown in FIG. 6 has been obtained by a principal component analysis of 47 published scales. FIGS. 7A-D are histograms illustrating random distributions of global linear hydrophobic moment magnitudes and relationship to four native moments that exhibit significant amphiphilicity.

Figure 8:
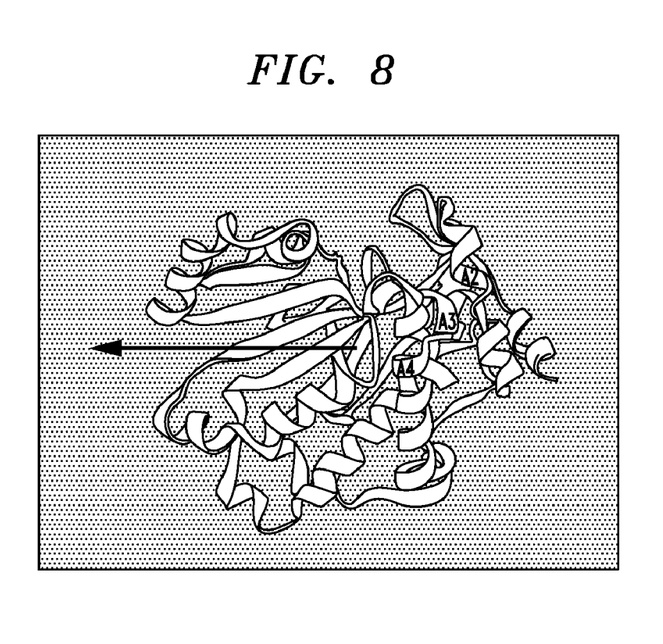
FIG. 8 is a molecular model illustrating direction of a global linear hydrophobic moment of protein 1AUA according to the teachings of the present invention.

The protein 1AUA, the yeast phosphatidyinositol-transfer protein exhibits catalytic activity between membrane layers. The carboxy-terminal forms the hydrophobic pocket of the phospholipid-binding domain. Six β-strands constitute the pocket floor. FIG. 8 is a molecular model illustrating direction of a global linear hydrophobic moment of protein 1AUA. The large global linear hydrophobic moment points in the direction of this pocket, as shown in FIG. 8, and away from the helices A2, A3 and A4. The moment vector is plotted with respect to the original PDB coordinates.

Figure 9:
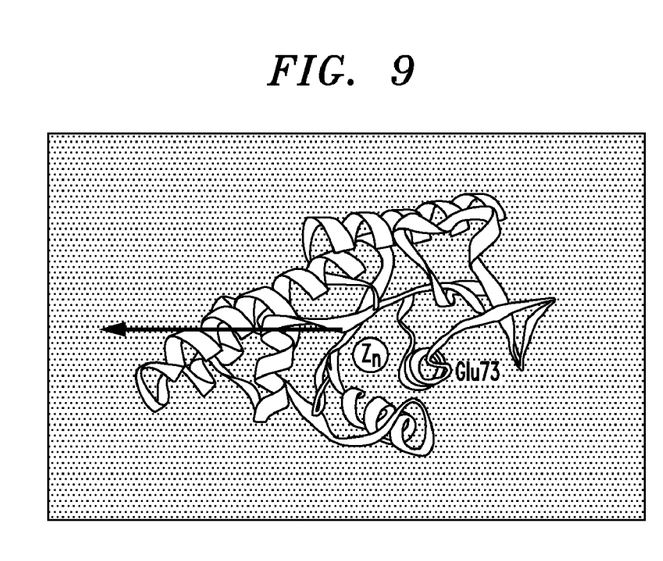
FIG. 9 is a molecular model illustrating direction of a global linear hydrophobic moment of protein 1DZV according to the teachings of the present invention.

The protein 1DZV, as well as the family of L-Fuculose-1-Phosphate Aldolase mutants, exhibit an enhanced degree of hydrophobic imbalance. These proteins are believed to belong to a superfamily of aldolases that catalyze carbon bond cleavage. FIG. 9 is a molecular model illustrating direction of a global linear hydrophobic moment of protein 1DZV. The calculated global linear hydrophobic moment points away from the amino end of the protein and the active site, which includes the zinc atom and the key catalytic acid/base residue, GLU 73, as shown in FIG. 9. There is an imbalance in residue hydrophobicity along the linear amino acid sequence of the protein. The first 85 residues from the amino end have an average value of hydrophobicity equal to −0.142, whereas, the remainder of the residues has an average value equal to 0.028. Consequently, the separated spatial locations of the residues at either of the ends of the protein contribute significantly to the orientation of the moment vector as well as to its amplified magnitude.

Another protein with enhanced magnitude hydrophobic moment is 2ACT, or actinidin. Actinidin is in the papain family, as is 1YAL, for example shown adjacent to actinidin in FIG. 5. Both proteins have 49 percent residue identity and a combinatorial expansion (CE) RMSD of 1.2 angstroms. The magnitudes of the global linear hydrophobic moments of 2ACT and 1YAL ale, however, different. Whereas 2ACT exhibits an enhanced value of the global linear hydrophobic moment, 1YAL has a global linear hydrophobic moment with a magnitude within the range of values obtained by randomizing the residue sequence. This difference highlights the independence of overall hydrophobic spatial organization with respect to protein structure.

The proteins, 1AKZ and 1UDH, are another example of two proteins with high sequence similarity and a CE RMSD of 1.4 angstroms that exhibit recognizably different residue hydrophobicity spatial arrangements. However, as expected, two proteins from different species in the same structural classification of proteins (SCOP) family with nearly 100 percent sequence identity and with a RMSD of 0.7 angstroms, for example, 1BN1 and the A chain of 1G6V, have magnitudes of the global linear hydrophobic moment that differ by eight percent.

Figure 10:
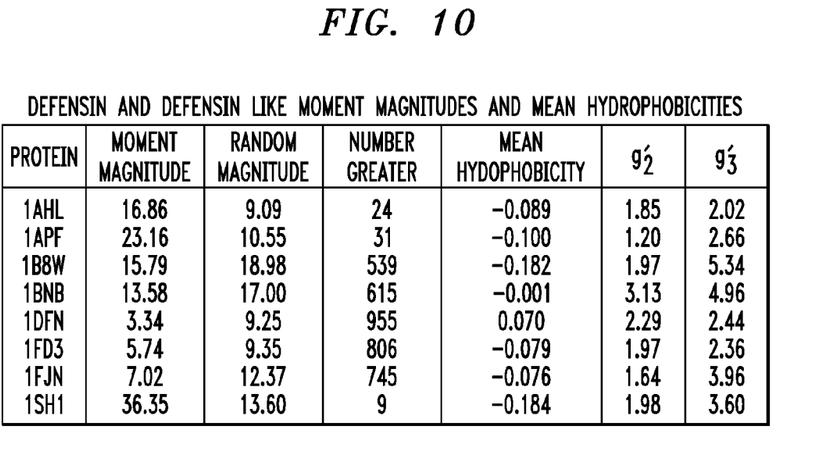
FIG. 10 is a table containing enhanced moment-of-geometry ratio values for defensin and defensin like protein structures.

Defensins are small antimicrobial proteins that act through the permeabilization of bacterial membranes. Since defensins attack the bacterial cell wall by residues that exhibit cationic and hydrophilic character; the spatial arrangement of residue hydrophobicity is of interest. FIG. 10 is a table containing enhanced moment-of-geometry ratio values for defensin and defensin like protein structures. FIG. 10 includes the neurotoxin, 1SH1, and two cardiac stimulants, 1AHL (Anthopleurin-B) and 1APF (Anthopleurin-A). Interestingly, of all eight structures, the neurotoxin and cardiac stimulants exhibit moment magnitudes that are significantly greater than the major fraction of the magnitudes randomly generated. The defensins, 1FD3 and 1DFN, are dimeric in a biologically active forms. While the CE aligned regions of 1FD3 and 1DFN, that do not include the α-helix of 1FD3, exhibit very different hydrophobic organization, the overall dimeric structures exhibit a correspondence in magnitude and direction of global linear hydrophobic moments.

FIG. 10 shows that whereas the global linear hydrophobic moment magnitude of 1AHL is comparable to the global linear hydrophobic moment magnitudes of 1B8W and 1BNB it exhibits a greater degree of amphipathicity than either 1B8W and 1BNB, relative to its global linear hydrophobic moment magnitude obtained by randomization of the amino acid location along the sequence. On average, protein structures will exhibit enhanced values of the average global linear hydrophobic moment when the protein shape deviates significantly from a sphere (sphericity), e.g., for structures such as 1B8W and 1BNB. Significant deviations from sphericity can be identified by enhanced values of the moment-of-geometry ratios, $g'_2$ and $g'_3$, provided in FIG. 10. For these structures, a greater percentage of residues reside at locations that are mapped to greater distances when mapping to a sphere. This greater percentage emphasizes that, particularly for small structures, the significance of the magnitude of the global linear hydrophobic moment should be evaluated relative to the average obtained from the randomization of amino acid location along the sequence. Consequently, 1AHL is considered to be more amphipathic than either 1B8W or 1BNB. Such correlation between the average global linear hydrophobic moment and deviation from sphericity is also generally noted from the entries of the tables in FIG. 3 and FIG. 4, above. These differences are, however, not as great as is shown in FIG. 10 since the deviations from sphericity are less for these larger structures.

Figure 11A:
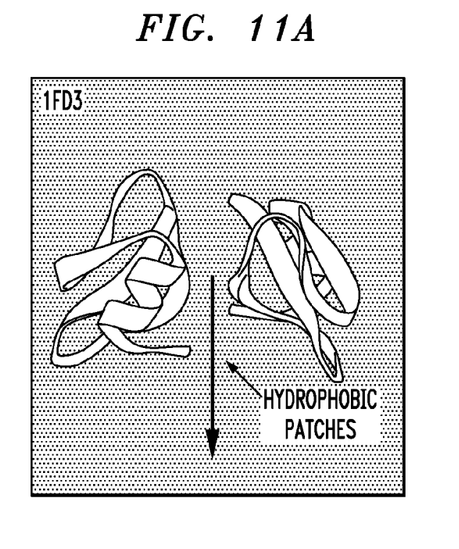
FIGS. 11A-B are molecular models illustrating the hydrophobic moment vectors of proteins 1FD3 and 1DFN according to the teachings of the present invention.
Figure 11B:
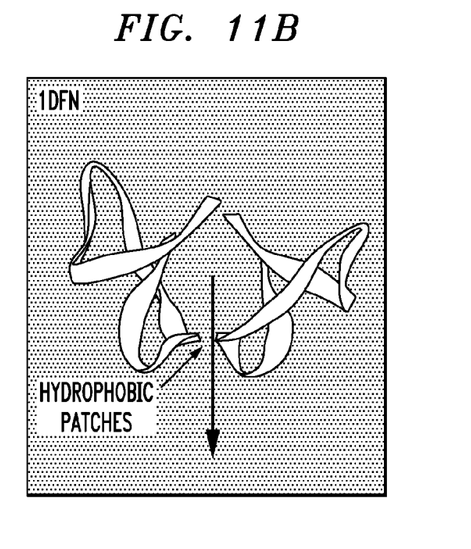

FIGS. 11A-B are molecular models illustrating the hydrophobic moment vectors of proteins 1FD3 and 1DFN. In FIGS. 11A-B, the molecular models of proteins 1FD3 and 1DFN, respectively, are superimposed upon the corresponding tertiary protein structure. Both vectors point in the direction of hydrophobic patches. For 1FD3, the vector points towards the center of the flat hydrophobic patches of the monomers. For 1DFN, the vectors point in the direction of the apolar base of the basket shaped dinner. The location of segregated patches of hydrophobic residues is important regarding issues involving the mechanism of defensin antimicrobial binding and activity.

Although illustrative embodiments of the present invention have been described herein, it is to be understood that the invention is not limited to those precise embodiments, and that various other changes and modifications may be made by one skilled in the art without departing from the scope or spirit of the invention.

What is claimed is:

1. A method for comparing at least two tertiary protein structures comprising a plurality of residues, for each tertiary protein structure, wherein the method is run on a system comprising one or more distinct devices, each of the one or more distinct devices being embodied on a tangible computer-readable recordable storage medium, the method comprising:

calculating a centroid of residue centroids, wherein calculating the centroid of residue centroids is carried out by a tertiary protein structure analyzer executing on a computer configured to carry out the step of calculating the centroid;

using the centroid of residue centroids as a spatial origin of a global linear hydrophobic moment;
calculating a first-order hydrophobic moment, wherein calculating the first-order hydrophobic moment is carried out by a tertiary protein structure analyzer executing on a computer configured to carry out the step of calculating the first-order hydrophobic moment;
enhancing correlation between residue centroid magnitude and residue solvent accessibility, wherein the correlation between residue centroid magnitude and residue solvent accessibility is enhanced using a distance metric, wherein enhancing correlation between residue centroid magnitude and residue solvent accessibility is carried out by a tertiary protein structure analyzer executing on a computer configured to carry out the step of enhancing correlation;
using the first-order hydrophobic moment and the enhanced correlation between residue centroid magnitude and residue solvent accessibility to define the global linear hydrophobic moment, wherein each of the residue centroids contributes a magnitude and direction to the global linear hydrophobic moment, the global linear hydrophobic moment characterizing an amphiphilicity of each tertiary protein structure, wherein the global linear hydrophobic moment is defined as $$\vec{h}_1 = \frac{1}{n}\sum_i h_i\left(x_i \hat{i} + \sqrt{g'_2}\, y_i \hat{j} + \sqrt{g'_3}\, z_i \hat{k}\right),$$

wherein $\vec{h}_1$ comprises the first-order hydrophobic moment given by the global linear hydrophobic moment, n comprises a total number of residues, $h_i$ comprises an origin of distribution, wherein the origin of distribution is the residue centroids, $x_i$, $y_i$ and $z_i$ comprise coordinates having the centroid of the residue centroids as the origin, $\hat{i}$, $\hat{j}$, and $\hat{k}$ comprise unit vectors along directions of principle axes used in the mapping of each ellipsoidal coordinate onto a sphere with radius equal to a principal axis, and $g'_2$ and $g'_3$ comprise scaled moments-of-geometry used to provide an ellipsoidal characterization of the protein structure via $g_1 x_p^2 + g_2 y_p^2 + g_3 z_p^2 = d^2$, wherein $g_1$, $g_2$ and $g_3$ are moments-of-geometry, $x_p$, $y_p$ and $z_p$ are coordinates in a frame of the principle axes with the centroid of the protein structure as origin and d is a distance measure, further wherein $x_{ip}^2 + g'_2 y_{ip}^2 + g'_3 z_{ip}^2 = d'^2_i$, with $g'_2 = g_2/g_1$; $g'_3 = g_2/g_1$; $d'^2 = d_i^2/g_1$, wherein $d'_i$ is a measure of radial fractional distance of the ith residue from the center of the protein to the protein surface, and wherein using the first-order hydrophobic moment and the enhanced correlation between residue centroid magnitude and residue solvent accessibility to define the global linear hydrophobic moment is carried out by a tertiary protein structure analyzer executing on a computer configured to carry out the step of using the first-order hydrophobic moment and the enhanced correlation between residue centroid magnitude and residue solvent accessibility to define the global linear hydrophobic moment;
using the global linear hydrophobic moment of each tertiary protein structure to compare the amphiphilicity of the at least two tertiary protein structures, wherein using the global linear hydrophobic moment of each tertiary protein structure to compare the amphiphilicity of the at least two tertiary protein structures is carried out by a tertiary protein structure analyzer executing on a computer configured to carry out the step of using the global linear hydrophobic moment of each tertiary protein structure to compare the amphiphilicity of the at least two tertiary protein structures; and
outputting the global linear hydrophobic moment and a result from comparing the amphiphilicity of the at least two tertiary protein structures to at least one of a user, a display, a memory and one or more additional computers on a network.

2. The method of claim 1, wherein the centroid of residue centroids represents a geometric center of the tertiary protein structure.

3. The method of claim 1, wherein the global linear hydrophobic moment characterizes a magnitude and a direction of amphiphilicity of the at least two tertiary protein structures.

4. The method of claim 1, wherein the global linear hydrophobic moment is used to determine a hydrophobic imbalance arising from interaction of the at least two tertiary protein structures with each other.

5. The method of claim 1, wherein the correlation between residue centroid magnitude and residue solvent accessibility is enhanced using an ellipsoidal metric.

6. The method of claim 1, wherein the correlation between residue centroid magnitude and residue solvent accessibility is enhanced using a solvent accessibility metric.

7. An apparatus for comparing at least two tertiary protein structures comprising a plurality of residues, for each tertiary protein structure, the apparatus comprising:
a memory; and
at least one processor operative to:
calculate a centroid of residue centroids;
use the centroid of residue centroids as a spatial origin of a global linear hydrophobic moment;
calculate a first-order hydrophobic moment;
enhance correlation between residue centroid magnitude and residue solvent accessibility, wherein the correlation between residue centroid magnitude and residue solvent accessibility is enhanced using a distance metric;
use the first-order hydrophobic moment and the enhanced correlation between residue centroid magnitude and residue solvent accessibility to define the global linear hydrophobic moment, wherein each of the residue centroids contributes a magnitude and direction to the global linear hydrophobic moment, the global linear hydrophobic moment characterizing an amphiphilicity of each tertiary protein structure, wherein the global linear hydrophobic moment is defined as $$\vec{h}_1 = \frac{1}{n}\sum_i h_i\left(x_i \hat{i} + \sqrt{g'_2}\, y_i \hat{j} + \sqrt{g'_3}\, z_i \hat{k}\right),$$

wherein $\vec{h}_1$ comprises the first-order hydrophobic moment given by the global linear hydrophobic moment, n comprises a total number of residues, $h_i$ comprises an origin of distribution, wherein the origin of distribution is the residue centroids, $x_i$, $y_i$ and $z_i$ comprise coordinates having the centroid of the residue centroids as the origin, $\hat{i}$, $\hat{j}$, and $\hat{k}$ comprise unit vectors along directions of principle axes used in the mapping of each ellipsoidal coordinate onto a sphere with radius equal to a principal axis, and $g'_2$ and $g'_3$ comprise scaled moments-of-geometry used to provide an ellipsoidal characterization of the protein structure via $g_1x_p^2+g_2y_p^2+g_3z_p^2=d^2$, wherein $g_1$, $g_2$ and $g_3$ are moments-of-geometry, $x_p$, $y_p$ and $z_p$ are coordinates in a frame of the principle axes with the centroid of the protein structure as origin and d is a distance measure, further wherein $x_{ip}^2+g'_2y_{ip}^2+g'_3z_{ip}^2=d'^2_i$, with $g'_2=g_2/g_1$; $g'_3=g_2/g_1$; $d'^2=d_i^2/g_1$, wherein $d'_i$ is a measure of radial fractional distance of the ith residue from the center of the protein to the protein surface;

use the global linear hydrophobic moment of each tertiary protein structure to compare the amphiphilicity of the at least two tertiary protein structures; and output the global linear hydrophobic moment and a result from comparing the amphiphilicity of the at least two tertiary protein structures to at least one of a user, a display, a memory and one or more additional computers on a network.

8. The apparatus of claim 7, wherein the centroid of residue centroids represents a geometric center of the tertiary protein structure.

9. The apparatus of claim 7, wherein the global linear hydrophobic moment characterizes a magnitude and a direction of amphiphilicity of the at least two tertiary protein structures.

10. The apparatus of claim 7, wherein the global linear hydrophobic moment is used to determine a hydrophobic imbalance arising from interaction of the at least two tertiary protein structures with each other.

11. The apparatus of claim 7, wherein the correlation between residue centroid magnitude and residue solvent accessibility is enhanced using an ellipsoidal metric.

12. The apparatus of claim 7, wherein the correlation between residue centroid magnitude and residue solvent accessibility is enhanced using a solvent accessibility metric.

13. An article of manufacture for comparing at least two tertiary protein structures comprising a plurality of residues, for each tertiary protein structure, comprising:

a non-transitory computer-readable recordable storage medium having computer-readable instructions tangibly embodied thereon which, when implemented, cause a computer to carry out a plurality of method steps comprising:

a step for calculating a centroid of residue centroids;

a step for using the centroid of residue centroids as a spatial origin of a global linear hydrophobic moment;

a step for calculating a first-order hydrophobic moment;

a step for enhancing correlation between residue centroid magnitude and residue solvent accessibility, wherein the correlation between residue centroid magnitude and residue solvent accessibility is enhanced using a distance metric;

a step for using the first-order hydrophobic moment and the enhanced correlation between residue centroid magnitude and residue solvent accessibility to define the global linear hydrophobic moment, wherein each of the residue centroids contributes a magnitude and direction to the global linear hydrophobic moment, the global linear hydrophobic moment characterizing an amphiphilicity of each tertiary protein structure, wherein the global linear hydrophobic moment is defined as $$\vec{h}_1 = \frac{1}{n}\sum_i h_i\left(x_i\hat{i} + \sqrt{g'_2}\,y_i\hat{j} + \sqrt{g'_3}\,z_i\hat{k}\right),$$

wherein $\vec{h}_1$ comprises the first-order hydrophobic moment given by the global linear hydrophobic moment, n comprises a total number of residues, $h_i$ comprises an origin of distribution, wherein the origin of distribution is the residue centroids, $x_i$, $y_i$ and $z_i$ comprise coordinates having the centroid of the residue centroids as the origin, $\hat{i}$, $\hat{j}$, and $\hat{k}$ comprise unit vectors along directions of principle axes used in the mapping of each ellipsoidal coordinate onto a sphere with radius equal to a principal axis, and $g'_2$ and $g'_3$ comprise scaled moments-of-geometry used to provide an ellipsoidal characterization of the protein structure via $g_1x_p^2+g_2y_p^2+g_3z_p^2=d^2$, wherein $g_1$, $g_2$ and $g_3$ are moments-of-geometry, $x_p$, $y_p$ and $z_p$ are coordinates in a frame of the principle axes with the centroid of the protein structure as origin and d is a distance measure, further wherein $x_{ip}^2+g'_2y_{ip}^2+g'_3z_{ip}^2=d'^2_i$, with $g'_2=g_2/g_1$; $g'_3=g_2/g_1$; $d'^2=d_i^2/g_1$; wherein $d'_i$ is a measure of radial fractional distance of the ith residue from the center of the protein to the protein surface;

a step for using the global linear hydrophobic moment of each tertiary protein structure to compare the amphiphilicity of the at least two tertiary protein structures; and a step for outputting the global linear hydrophobic moment and a result from comparing the amphiphilicity of the at least two tertiary protein structures to at least one of a user, a display, a memory and one or more additional computers on a network.

14. The article of manufacture of claim 13, wherein the centroid of residue centroids represents a geometric center of the tertiary protein structure.

15. The article of manufacture of claim 13, wherein the global linear hydrophobic moment characterizes a magnitude and a direction of amphiphilicity of the at least two tertiary protein structures.

16. The article of manufacture of claim 13, wherein the global linear hydrophobic moment is used to determine a hydrophobic imbalance arising from interaction of the at least two tertiary protein structures with each other.

17. The article of manufacture of claim 13, wherein the correlation between residue centroid magnitude and residue solvent accessibility is enhanced using an ellipsoidal metric.

18. The article of manufacture of claim 13, wherein the correlation between residue centroid magnitude and residue solvent accessibility is enhanced using a solvent accessibility metric.

\* \* \* \* \*